United States Patent
Hsu et al.

[19]

[11] Patent Number: 6,091,990
[45] Date of Patent: Jul. 18, 2000

[54] SYSTEM FOR GROUPING AND DISPLAYING CARDIAC ARRHYTHMIA DATA

[75] Inventors: William Hsu, Circle Pines; Douglas J. Lang, Arden Hills, both of Minn.

[73] Assignee: Cardiac Pacemakers, Inc., St. Paul, Minn.

[21] Appl. No.: 09/432,694

[22] Filed: Nov. 3, 1999

Related U.S. Application Data

[62] Division of application No. 09/047,647, Mar. 25, 1998, Pat. No. 6,016,442.

[51] Int. Cl.⁷ ..................................................... A61N 1/37
[52] U.S. Cl. .................................................. 607/5; 607/27
[58] Field of Search .............................. 607/4, 5, 27, 31, 607/59, 61; 600/510

[56] References Cited

U.S. PATENT DOCUMENTS

| | | | |
|---|---|---|---|
| 4,800,883 | 1/1989 | Winstrom | 128/419 D |
| 4,809,697 | 3/1989 | Causey, III et al. | 607/31 |
| 4,825,869 | 5/1989 | Sasmor et al. | 607/27 |
| 4,850,357 | 7/1989 | Bach, Jr. et al. | 128/419 |
| 4,964,410 | 10/1990 | Leahey et al. | 128/696 |
| 4,998,531 | 3/1991 | Bocchi et al. | 128/419 |
| 5,111,816 | 5/1992 | Pless et al. | 128/419 |
| 5,129,392 | 7/1992 | Bardy et al. | 128/419 |
| 5,215,083 | 6/1993 | Drane et al. | 128/419 D |
| 5,217,021 | 6/1993 | Steinhaus et al. | 128/702 |
| 5,279,293 | 1/1994 | Andersen et al. | 607/5 |
| 5,292,341 | 3/1994 | Snell | 607/30 |
| 5,311,874 | 5/1994 | Baumann et al. | 128/705 |
| 5,312,441 | 5/1994 | Mader et al. | 607/5 |
| 5,411,530 | 5/1995 | Akhtar | 604/14 |
| 5,421,830 | 6/1995 | Epstein et al. | 607/30 |
| 5,513,645 | 5/1996 | Jacobson et al. | 128/710 |
| 5,549,654 | 8/1996 | Powell | 607/32 |
| 5,607,460 | 3/1997 | Kroll et al. | 607/30 |

FOREIGN PATENT DOCUMENTS

| | | | |
|---|---|---|---|
| 0491649 | 6/1992 | European Pat. Off. | A61N 1/39 |
| 0558353 | 9/1993 | European Pat. Off. | A61N 1/39 |
| 0565084 | 10/1993 | European Pat. Off. | |
| 0711531 | 5/1996 | European Pat. Off. | |

*Primary Examiner*—William E. Kamm
*Attorney, Agent, or Firm*—Schwegman, Lundberg, Woessner & Kluth, P.A.

[57] ABSTRACT

A medical device system and method of plotting symbols representing complexes of selected arrhythmic events on an interactive display screen, for organizing, displaying and interacting with a patient's recorded arrhythmia episodes. Stored arrhythmic episode are selected from a plurality of arrhythmic episodes, where the stored arrhythmic episode having a plurality of complexes. A similarity value and a dissimilarity value is calculated for each complex of the plurality of complexes of the selected arrhythmic episode with respect to normal sinus rhythm complexes. Symbols representing the arrhythmic complexes are then plotted as a function of the calculated similarity values and the dissimilarity values on an interactive display screen. Additional information relating to the arrhythmic event is elicited through interacting with the symbols displayed on the interactive display screen.

5 Claims, 10 Drawing Sheets

SYSTEM FOR GROUPING AND DISPLAYING CARDIAC ARRHYTHMIA DATA

CROSS-REFERENCE TO RELATED APPLICATIONS

This application is a division of U.S. patent application Ser. No. 09/047,647, filed on Mar. 25, 1998, now U.S. Pat. No. 6,016,442, which is incorporated herein by reference.

TECHNICAL FIELD

The present invention relates generally to medical devices and in particular to a system for organizing, displaying and interacting with cardiac arrhythmia data.

BACKGROUND OF INVENTION

Implantable cardiac defibrillators (ICDs) are well established therapeutic devices for treating patients who have experienced one or more documented episodes of hemodynamically significant ventricular tachycardia or ventricular fibrillation. Since their clinical inception more than two decades ago, ICDs have evolved from basic to sophisticated electronic devices that provide physicians with a variety of clinically useful functions with which to treat patients.

Presently, even the most basic of ICDs typically has more than one tachycardia detection criterion, tiered therapy which combines bradycardia support pacing with various antitachycardia pacing modes, low-energy cardioversion, defibrillation, and data logging capabilities. The data logging capabilities within ICDs have become increasingly important, since the amount of data required for the ICDs operation increases proportionally with the increase in ICD functions. Efficiently processing this large amount of data has become possible with the incorporation of microprocessors and memory within the ICD.

Even with the advances in ICD data logging and processing capabilities, arrhythmia event recording capabilities have been limited, making it difficult to verify the adequacy and efficacy of arrhythmia detection and therapy settings. Furthermore, ICDs have been designed to record electrocardiogram and diagnostic channel data which can indicate to the physician the ICDs behavior during multiple tachyarrhythmia episodes. These ICDs also include arrhythmic event counters which log the number of episodes detected and the success or failure of each programmed therapy. Moreover, monitoring capability in some ICDs allow for recording of electrocardiogram waveforms, which can assist the physician in assessing the efficacy of the implanted ICD.

Once an ICD has been implanted, the physician interacts with the ICD through a clinical programmer. The clinical programmer is used to establish a telemetric link with the implanted ICD. The telemetric link allows for instructions to be sent to the electronic circuitry of the ICD and clinical data regarding the occurrence and treatment of a patient's cardiac arrhythmias and the ICD's operation to be sent from the electronic circuitry of the ICD to the clinical programmer. The typical programmer is a microprocessor-based unit that has a wand for creating the telemetric link between the implanted ICD and the programmer, and a graphics display screen that presents a patient's recorded cardiac data and ICD system information to the physician.

As the amount of cardiac data recorded by ICDs increases with each new generation of ICD, manufacturers and clinicians alike are becoming more sensitive to the role that time-efficient programming and data interpretation plays in the physician's clinical visit with the patient. As ICDs become increasingly complex, the interpretation of recorded arrhythmic episodes and the programming of the ICD can be challenging and time-consuming tasks for some users. Therefore, a need exists for improved ICD and programmer technology that will provide efficient classification and presentation of ICD recorded arrhythmic data to assist a physician in programming and interpreting an implanted ICD's functions.

SUMMARY OF THE INVENTION

The present disclosure describes a medical device system for organizing, displaying and interacting with a patient's recorded arrhythmia episodes. In one embodiment, the medical device system graphically displaying symbols representing one or more arrhythmic episodes on an interactive display screen based on at least one arrhythmia analysis criteria. The symbols representing the one or more arrhythmic episodes are displayed on an interactive display screen or interface, on which a physician reviews not only the cumulative number of arrhythmic episodes that the patient has experienced, but also the morphological similarities of the episodes. Additionally, the physician is also able to review the recorded electrocardiogram and therapy regimens delivered in order to treat a given arrhythmia. By displaying the patient's recorded cardiac arrhythmic episodes on an interactive display screen, the physician can more quickly assess and interpret the nature of the patient's cardiac arrhythmias and provide for more effective and efficient programming of the patient's ICD.

In one embodiment, the medical device system comprises a cardiac defibrillator and a medical device programmer unit for the cardiac defibrillator. The cardiac defibrillator includes electronic control circuitry for determining and recording the occurrence of arrhythmic episodes of a heart. The programmer unit has programmer electronic circuitry coupled to an interactive display screen. In one embodiment, the programmer electronic circuitry is coupled to the electronic control circuitry of the cardiac defibrillator through a telemetric link. This allows for cardiac data to be received from, and programming signals to be sent to, the cardiac defibrillator.

After receiving the stored cardiac data, the programmer displays a therapy history of the plurality of arrhythmic episodes detected and treated by the cardiac defibrillator on the interactive display screen. One or more of the stored plurality of arrhythmic episodes is selected through the interactive display screen, along with at least one arrhythmia analysis criteria. In one embodiment, the arrhythmia analysis criteria include a similarity/dissimilarity determination, a chronological occurrence of arrhythmias, a circadian occurrence of arrhythmia, morphological similarities, arrhythmia rate, therapy outcome, therapy type, and/or sensor reading. The programmer then graphically displays symbols representing the selected arrhythmic episodes on the interactive display screen based on the at least one arrhythmia analysis criteria.

In one embodiment, the programmer graphically displays distinct symbols representing each of the selected one or more arrhythmic episodes as a function of time. In an alternative embodiment, the programmer plots the selected arrhythmic episodes using a similarity/dissimilarity determination. The programmer electronic circuitry determines an arrhythmic vector for each of the plurality of arrhythmic complexes based on received cardiac QRS waves. Each arrhythmic vector is then compared with a normal rhythm vector representing a patient's QRS complex during normal sinus rhythm to calculate a similarity value and a dissimilarity value for each of the arrhythmic complexes. A symbol representing each of the plurality of complexes of the selected arrhythmic episodes is then generated by the programmer. The programmer then plots, or maps, one or more of the symbols representing the arrhythmia complexes as a function of the calculated similarity values and the dissimilarity values on an interactive display screen. In one embodiment, the symbols are plotted on a discrimination plane having a similarity coordinate axis and a dissimilarity coordinate axis which are orthogonal to the similarity coordinate axis.

In an additional embodiment, symbols representing the arrhythmia complexes of one or more arrhythmic episodes are grouped together within a defined boundary created on the interactive display screen. In one embodiment, the defined boundary is drawn by the user on the interactive display screen. In an alternative embodiment, the defined boundary is created by the electronic control circuitry programmed to distinguish discrete regions of plotted, or mapped, symbols. The position of the defined boundaries encircling the symbols is then retrievably stored.

The stored boundary positions are retrieved at the request of the user. In one embodiment, the user selectively designates one or more boundaries as a notice boundary. The medical device programmer plots the retrieved notice boundaries and symbols representing subsequent arrhythmic complexes on the interactive display screen. Notice boundaries cause the programmer to display a notice on the interactive display screen if at least one symbol representing one or more arrhythmic episodes fall within one or more of the defined notice boundaries.

In an additional embodiment, the programmer also retrievably stores a representative electrocardiogram signal of one or more arrhythmic episodes contained within the defined boundaries. The stored representative electrocardiogram signal is then displayed when the user selects a defined boundary of interest. In this way, the user can review the electrocardiogram signal of stored arrhythmic episodes from the patient's previous visits, and allows the user to update the electrocardiographic information if necessary. In an additional embodiment, the programmer also retrievably stores therapy regimens delivered to treat each of the one or more arrhythmic episodes, and the time at which each of the one or more arrhythmic episodes occurred.

In an additional embodiment, the user selects one of the distinct symbol representing at least one arrhythmic episode on the interactive display screen and requests that one or more channels of the recorded electrocardiogram of the arrhythmic event be displayed on the interactive display screen. In one embodiment, both the graphical display of the selected arrhythmic episodes and the selected electrocardiogram are simultaneously displayed on the interactive display screen. In an alternative embodiment, the user selects one of the distinct symbols representing an arrhythmic event on the interactive display screen and requests information relating to the therapy regimen provided to treat the selected arrhythmic episode be displayed on the interactive display screen. In one embodiment, this informational message includes a history of the type of therapy provided to convert the arrhythmia, along with any information on posttherapy redetection.

In an additional embodiment, the user tests the effects of changing a programmable parameter of a cardiac defibrillator by running a simulation of the changed programmable parameter in the medical device programmer. In one embodiment, the user would identify one or more mistakenly treated arrhythmias on the interactive display screen. The user then makes changes to one or more of the cardiac defibrillator's programmable parameters in the programmer. A simulation algorithm is then run to tests the effect of the parameter changes using the retrieved cardiac data. From the results of the simulation, the user can determine if appropriately treated arrhythmias would have received treatment and the mistakenly treated arrhythmia would have failed to receive treatment under the simulation in the programmer.

BRIEF DESCRIPTION OF DRAWING

In the drawings, where like numerals describe like components throughout the several views.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments of the present invention illustrated herein are described as being included in an implantable cardiac defibrillator, which may include numerous pacing modes known in the art, and an external medical device programmer. However, the medical system and method of the present invention could also be implemented in an external cardioverter/monitor system as are known in the art. Also, the medical system and method of the present invention could also be implemented in an implantable atrial cardioverter-defibrillator, which may include numerous pacing modes known in the art. Furthermore, although the present invention is described in conjunction with an implantable defibrillator having a microprocessor based architecture, it will be understood that the implantable cardiac defibrillator (or other implanted device) may be implemented in any logic based, custom integrated circuit architecture, if desired.

Figure 1:
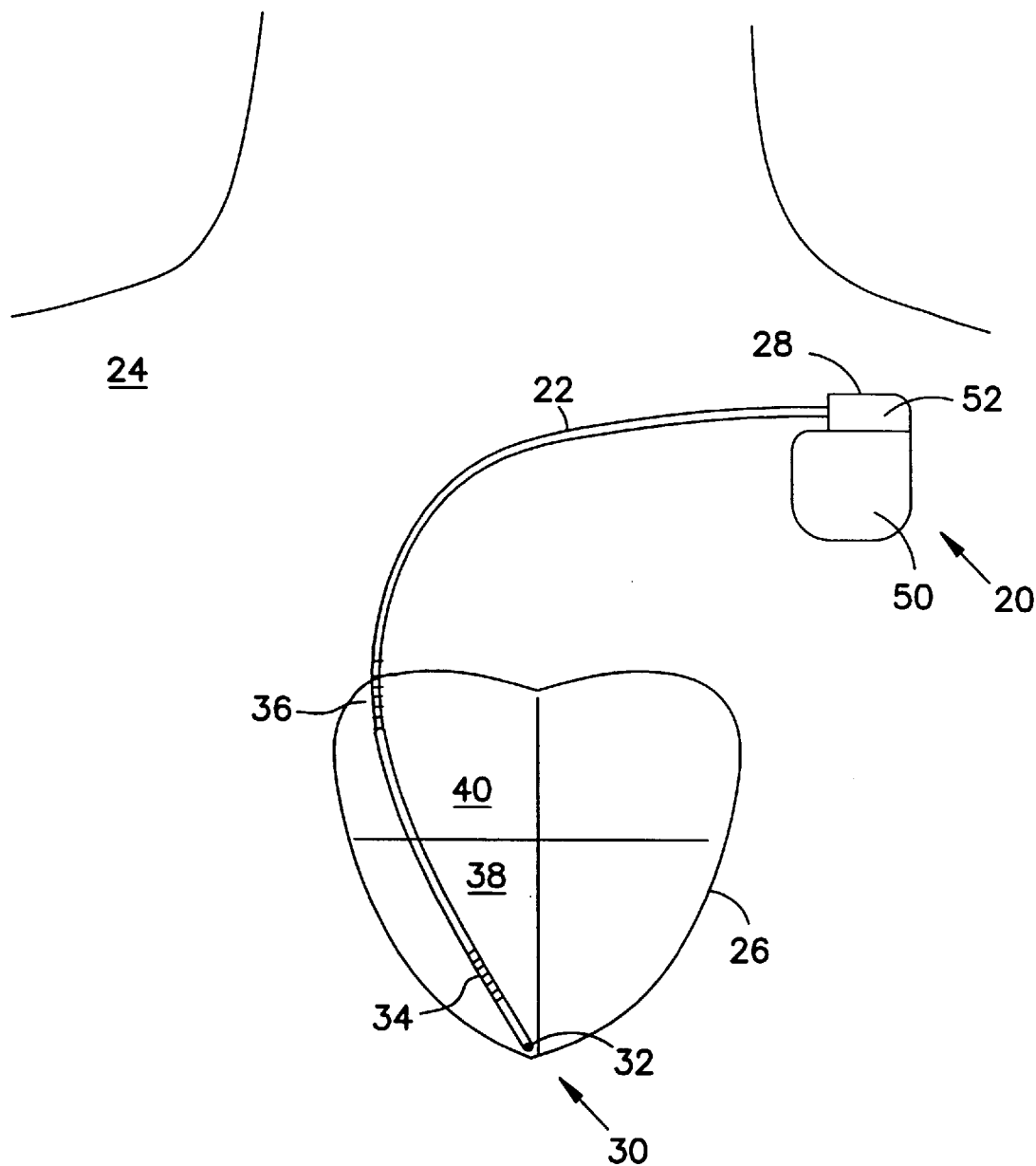
FIG. 1 is an embodiment of an implantable cardiac defibrillator implanted into a heart of a patient, from which portions have been removed to show detail.

Referring now to FIGS. 1 of the drawings, there is shown one embodiment of a medical device system which includes an implantable cardiac defibrillator 20 electrically and physically coupled to at least one intracardiac catheter 22. In one embodiment, the intracardiac catheter 22 includes one or more pacing electrodes and one or more intracardiac defibrillation electrodes.

The intracardiac catheter 22 is implanted in a human body 24 with portions of the intracardiac catheter 22 inserted into a heart 26 to detect and analyze electric cardiac signals produced by the heart 26 and to provide electrical energy to the heart 26 under certain predetermined conditions to treat cardia arrhythmias, including ventricular fibrillation, of the heart 26.

In one embodiment, the intracardiac catheter 22 is an endocardial lead adapted to be releasably attached to the cardiac defibrillator 20. The intracardiac catheter 22 has an elongate body with a proximal end 28 and a distal end 30 and is shown as having a pacing electrode 32 located at, or adjacent, the distal end 30 of the intracardiac catheter 22. In one embodiment, the pacing electrode 32 is a tip electrode positioned at the distal end 30 of the intracardiac catheter 22. Alternatively, the pacing electrode 32 is an annular, or a semi-annular ring electrode positioned adjacent the distal end 30.

The intracardiac catheter 22 also includes one or more defibrillation electrodes. In one embodiment, the intracardiac catheter 22 has a first defibrillation electrode 34 and a second defibrillation electrode 36, where the first defibrillation electrode 34 and the second defibrillation electrode 36 are defibrillation coil electrodes as are known in the art. The first defibrillation electrode 34 is spaced apart and proximal from the pacing electrode 32, and the second defibrillation electrode 36 is spaced apart and proximal from the first defibrillation electrode 34 such that when the intracardiac catheter 22 is positioned within the heart 26 the pacing electrode 32 and the first defibrillation electrode 34 reside within a right ventricle 38 of the heart 26, with the pacing electrode 32 in an apex location within the right ventricle 38, and the second defibrillation electrode 36 is positioned within the right atrium chamber 40 of the heart 26 or a major vein leading to the right atrium chamber 40 of the heart 26.

Figure 2:
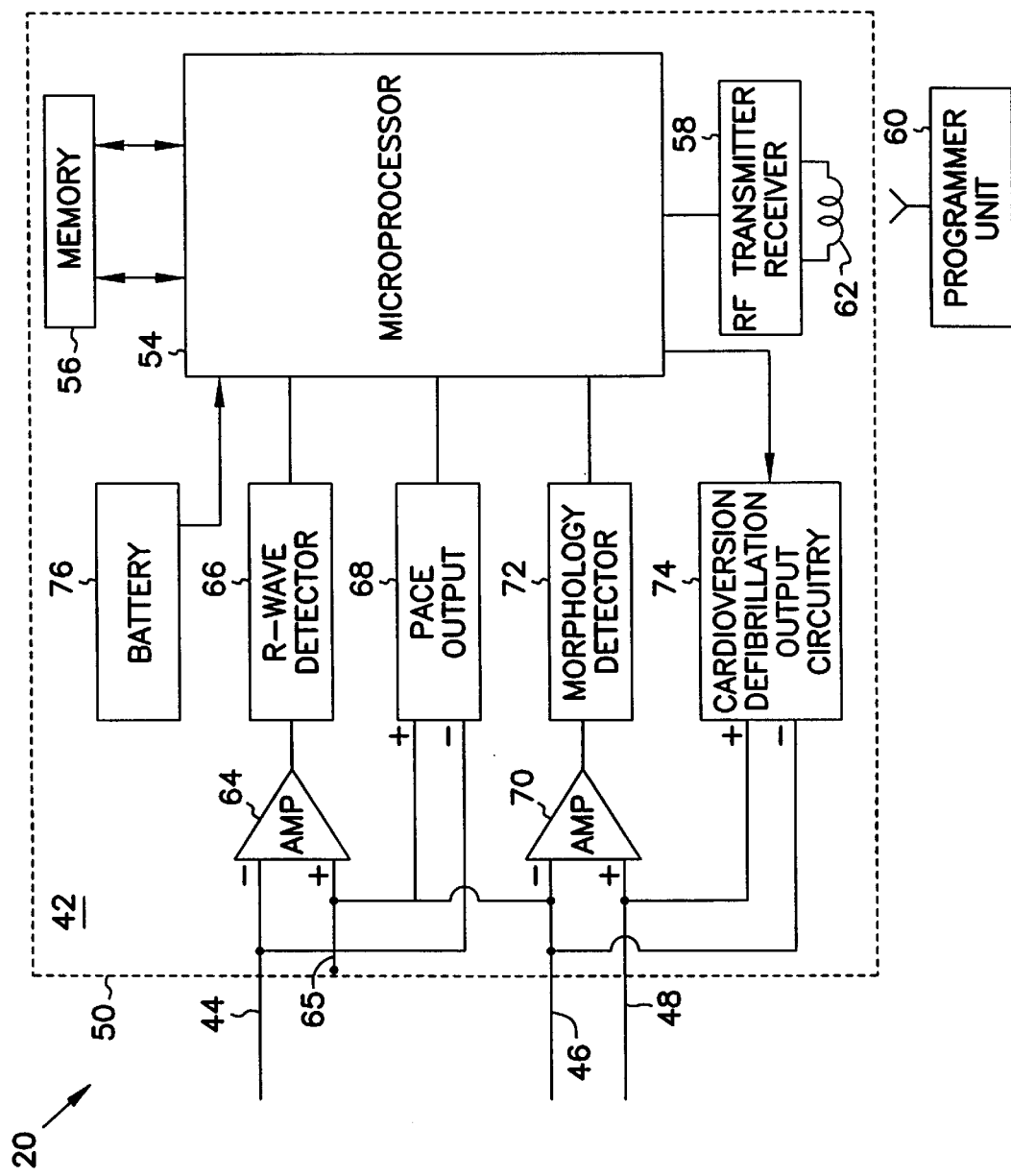
FIG. 2 is a block diagram of an implantable cardiac defibrillator according to one embodiment of the present invention.

Referring now to FIG. 2, there is shown an embodiment of a block diagram of a cardiac defibrillator 20. The cardiac defibrillator 20 includes electronic control circuitry 42 for receiving cardiac signals from a heart 26 and delivering electrical energy to the heart 26. The electronic control circuitry 42 includes terminals, labeled with reference numbers 44, 46, and 48 for connection to electrodes attached to the surface of the intracardiac catheter 22. The pacing electrode 32 is electrically connected to terminal 44 and to the electronic control circuitry 42 through an electrically insulated conductor provided within the elongate body of the intracardiac catheter 22. The first defibrillation electrode 34 and the second defibrillation electrode 36 are connected to terminals 46 and 48, respectively, and to the electronic control circuitry 42 through electrically insulated conductors provided within the elongate body of the intracardiac catheter 22.

In one embodiment, the electronic control circuitry 42 of the cardiac defibrillator 20 is encased and hermetically sealed in a housing 50 suitable for implanting in a human body. In one embodiment, titanium is used for the housing 50, however, other biocompatible housing materials as are known in the art may be used. A connector block 52 is additionally attached to the housing 50 of the cardiac defibrillator 20 to allow for the physical and the electrical attachment of the intracardiac catheter 22 and the electrodes to the cardiac defibrillator 20 and the encased electronic control circuitry 42.

The electronic control circuitry 42 of the cardiac defibrillator 20 is a programmable microprocessor-based system, with a microprocessor 54 and a memory circuit 56, which contains parameters for various pacing and sensing modes and stores data indicative of cardiac signals received by the electronic control circuitry 42. In one embodiment, data stored in the memory circuit 56 includes arrhythmia episode details, such as: a raw electrocardiogram signals, including two or more channels such as a ventricular signal and an atrial signal; a chronological number of the episode; the date and time of the episode; the type of episode detected; the onset rate of the episode; the stability of the episode; the duration of the episode; pre-therapy and post-therapy average atrial and ventricular rates; and the type of therapy delivered. Other arrhythmia episode data known in the art can also be recorded and stored in the memory circuit 56.

A transmitter circuit 58 is additionally coupled to the electronic control circuitry 42 and the memory circuit 56 to allow the cardiac defibrillator 20 to communicate with a programmer unit 60. In one embodiment, the transmitter circuit 58 and the programmer unit 60 use a wire loop antenna 62 and a radio frequency telemetric link, as is known in the art, to receive and transmit signals and data to and from the programmer unit 60 and the electronic control circuitry 42. In this manner, programming commands or instructions are transferred to the microprocessor 54 of the cardiac defibrillator 20 after implant, and stored cardiac data pertaining to sensed arrhythmic episodes within the heart 26 and subsequent therapy, or therapies, applied to correct the sensed arrhythmic event are transferred to the programmer unit 60 from the cardiac defibrillator 20.

The embodiment of the cardiac defibrillator block diagram shows the pacing electrode 32 coupled to a sense amplifier 64. In an additional embodiment, the housing 50 of the cardiac defibrillator 20 is also coupled to the sense amplified 64 at 65 to allow for unipolar cardiac rate sensing between the pacing electrode 32 and the housing 50 of the cardiac defibrillator 20. The output of the sense amplifier 64 is shown connected to an R-wave detector 66. These components serve to sense and amplify the QRS waves of the heart, and apply signals indicative thereof to the microprocessor 54. Among other things, microprocessor 54 responds to the R-wave detector 66 by providing pacing signals to a pace output circuit 68, as needed according to the programmed pacing mode. Pace output circuit 68 provides output pacing signals to terminals 44 and 65, which connect to the pacing electrode 32 and the housing 50 of the cardiac defibrillator 20, for cardiac pacing.

The first defibrillation electrode 34 and the second defibrillation electrode 36 are coupled to a sense amplifier 70, whose output is connected to a cardiac morphology detector 72. These components serve to sense and amplify the QRS-waves of the cardiac cycle from the ventricular region of the heart 26, and apply signals indicative thereof to the microprocessor 54. In one embodiment, the cardiac morphology detector 72 includes an analog filter for filtering cardiac signal noise sensed by the electrodes. The cardiac signals are then bandlimited before arriving at an analog-to-digital filter. The cardiac signals are then A/D converted into a digital signal and subsequently received by the microprocessor 54. In an alternative embodiment, the cardiac signals are filtered through an analog peak detector to extract the maximum and minimum cardiac signal values for each sensed cardiac interval.

The microprocessor 54 responds to the cardiac signals sensed within the heart 26 using the intracardiac catheter 22 by providing signals to cardioversion/defibrillation output circuitry 74 to provide either cardioversion or defibrillation electrical energy to the heart 26 depending upon nature of the arrhythmia sensed by the cardiac defibrillator 20. Power to the cardiac defibrillator 20 is supplied by an electrochemical battery 76 that is housed within the cardiac defibrillator 20.

Figure 3:
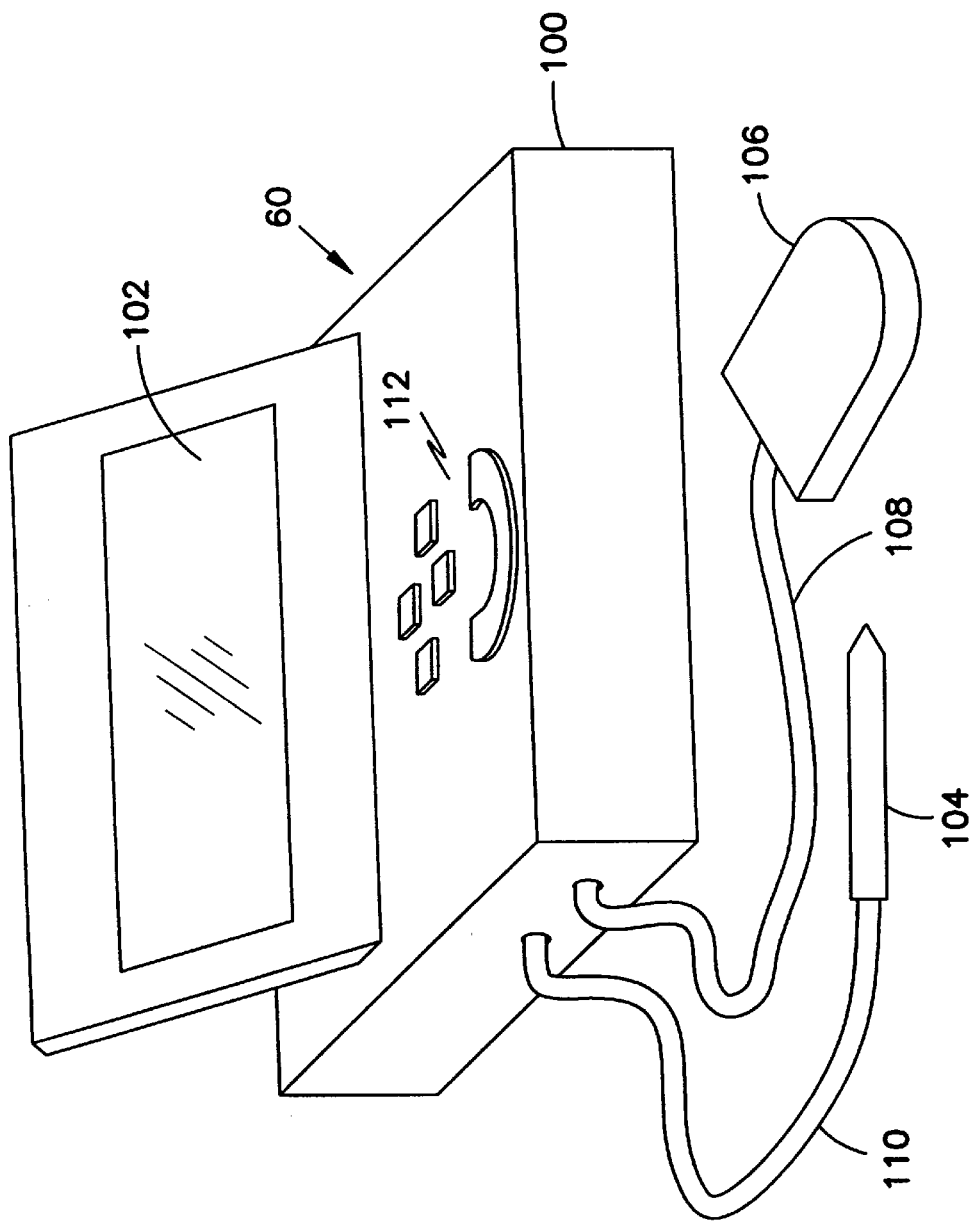
FIG. 3 is a perspective view of an external programming unit according to one embodiment of the present invention which is used for communicating with the implantable cardiac defibrillator of FIG. 1.

Referring now to FIG. 3, there is shown one embodiment of a medical device programmer 60 of the medical device system. As previously mentioned, one embodiment of the medical device programmer 60 for the implantable cardiac defibrillator 20 takes the form of an external controller as are known in the art. However, in an alternative embodiment, the medical device system is a completely external device such as an external cardioverting/defibrillator system as are known in the art, where the programmer unit is physically and electronically integrated into electronic control circuitry similar to the electronic control circuitry 42 of the cardiac defibrillator 20. An example of this latter embodiment is for an external cardiac monitor and defibrillation unit, electrically connected to the heart by any combination of intracardiac catheters, epicardial electrodes and/or externally cardiac electrodes, all of which are known in the art.

FIG. 3 shows one embodiment of a medical device programmer 60 designed to be positioned external of the human body 24 for communicating with an implantable medical device, such as the cardiac defibrillator 20 from FIG. 1, via RF telemetry. The medical device programmer 60 has programmer electronic circuitry, including a microprocessing unit and related circuitry, such as digital memory, which is coupled to a graphics display screen 102.

In one embodiment, the medical device programmer 60 comprises an outer housing 100 which is made of a thermal plastic or other suitable lightweight durable material. The graphics display screen 102 is disposed on the upper surface of housing 100. The graphics display screen 102 folds down into a closed position when medical device programmer 60 is not in use, thereby reducing the size of medical device programmer 60 and protecting the display surface of graphics display screen 102 during transportation and storage.

In an additional embodiment, the external programmer additionally has a floppy disk drive and a hard drive disposed within the housing. Air vents are provided at various points in the housing 100 so that an internal fan can circulate air within the housing 100 and prevent overheating of components therein.

The medical device programmer 60 is shown with the graphics display screen 102 positioned in one of a plurality of possible open positions such that a display on the graphics display screen 102 is visible to a user situated in front of the medical device programmer 60. In one embodiment, the graphics display screen 102 is of the LCD or electroluminescent type. The graphics display screen 102 is operatively coupled to the electronic circuitry disposed with the housing 100 and is adapted to provide a visual display of graphics and/or data under control of the programmer electronic circuitry.

The medical device programmer 60 further includes a user input device coupled to the electronic circuitry. In one embodiment, the user input device is the graphics display screen 102, which is provided with touch-sensitive capability, such that a user can interact with the programmer electronic circuitry by touching the display area on the graphics display screen 102 with a stylus 104, or even the user's finger. In one embodiment, the touch-sensitive graphics display screen is primary input for the medical device programmer 60. The medical device programmer 60 further includes a programming head 106, which is place over a patient's body near the implant site of an implanted device, such as the cardiac defibrillator 20, in order to establish a telemetry link between the cardiac defibrillator 20 and the medical device programmer 60. The telemetry link between the cardiac defibrillator 20 and the medical device programmer 60 allows the electronic circuitry coupled to the graphics display screen to be coupled to the electronic control circuitry of the cardiac defibrillator 20. The programming head 106 is coupled to the electronic circuitry of medical device programmer 60 and a receiver circuit for receiving signals from the transmitter circuit indicative of cardiac signals by a cable 108.

The stylus 104 used to interact with the touch-sensitive graphics display screen 102 is coupled to the programmer electronic circuitry within the housing 100 by a cable 110. Alternatively, the medical device programmer 60 may be equipped with a conventional computer "mouse"-type pointing device, rather than a stylus. In the absence of either a stylus or a mouse, on-screen cursor control for enabling user interaction with medical device programmer 60 may be facilitated through cursor control keys 112 (arrow keys or the like) disposed on the medical device programmer 60.

The medical device programmer 60 further includes a receiver circuit for receiving signals from the transmitter circuit indicative of cardiac signals. Through the telemetric contact with the cardiac defibrillator 20, the medical device programmer 60 is capable of capturing and storing recorded electrocardiogram data transmitted from the cardiac defibrillator 20 and displaying the electrocardiogram data on its graphics display screen 102.

Figure 4:
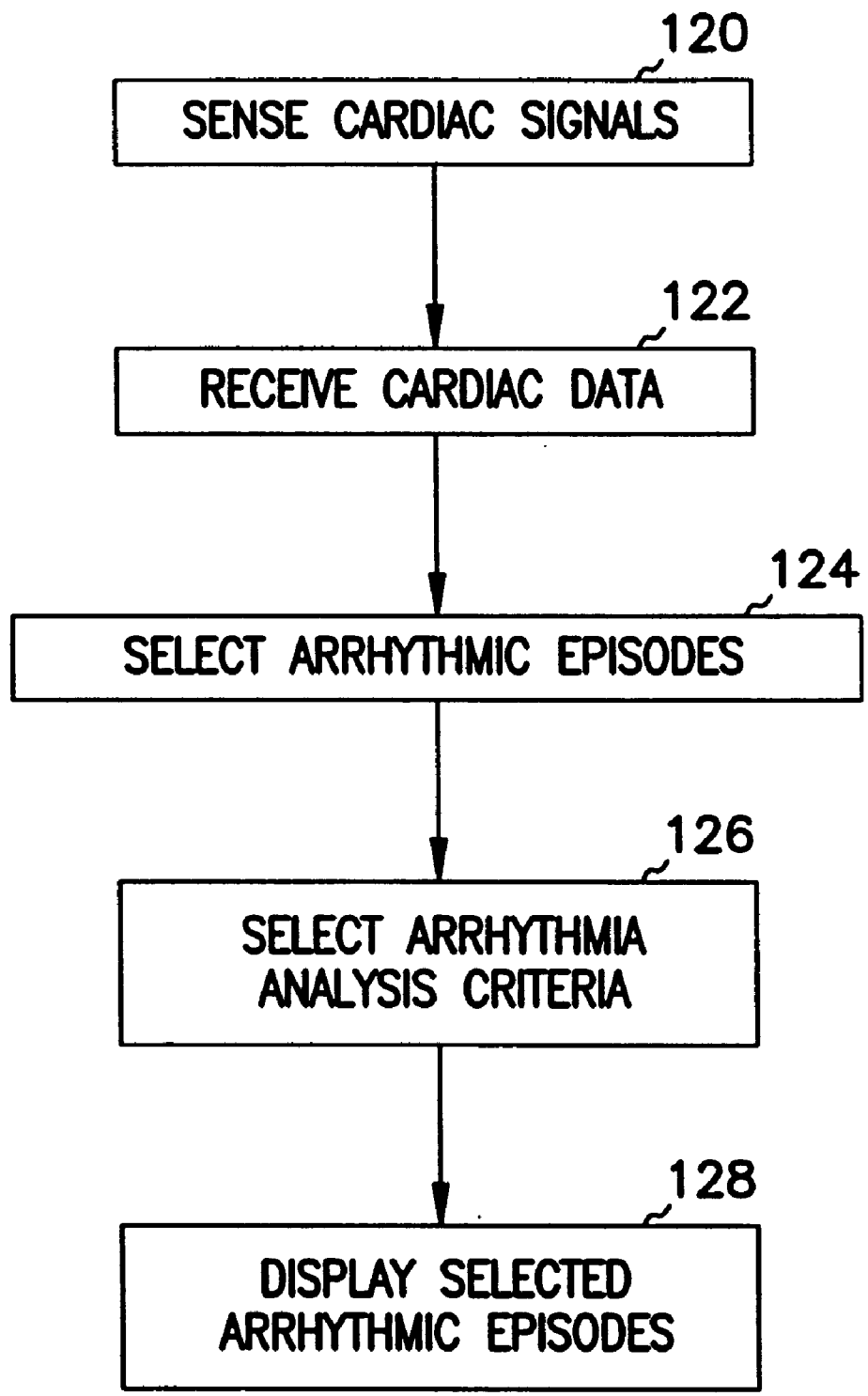
FIG. 4 is a flow diagram illustrating one embodiment of the present invention.

Referring now to FIG. 4, there is shown a flow diagram of one embodiment of the present invention. At step 120, the cardiac defibrillator 20 senses, electronically records signals representing arrhythmic episodes and provides therapy for arrhythmic episodes experienced by a patient. In one embodiment, the implantable cardiac defibrillator 20 electronically records arrhythmic episodes and stores detail on the arrhythmic episodes in its memory. The medical device programmer 60 is used to interrogate the implanted cardiac defibrillator 20 at step 122. During the interrogation, cardiac data, including information related to recorded arrhythmic episodes, is transferred from the electronic control circuitry 42 and received by the electronic circuitry of the medical device programmer 60 for analysis and display. In one embodiment, the medical device programmer 60 receives the cardiac data through the use of a telemetric link. In addition to receiving arrhythmic cardiac data, the implantable cardiac defibrillator 20 also provides cardiac data on "snapshots" of the patient's normal sinus rhythms, where the snapshots are brief portions of normal sinus rhythm electrocardiogram recordings. Typically, these normal sinus rhythm "snapshots" are sensed, recorded and stored in the cardiac defibrillator 20 under the supervision and control of the patient's physician.

In one embodiment, after downloading the stored cardiac data from the implanted cardiac defibrillator, the medical device programmer 60 displays a summary of the recorded arrhythmic events in a therapy history display. This is typically a chronological textual list of a plurality of arrhythmic events recorded by the cardiac defibrillator. The summary of the recorded arrhythmic events includes, but is not limited to, arrhythmia episode details, such as the electrocardiogram signals, the chronological number of the episode, the date and time of the episode, the type of episode detected, the onset rate of the episode, the stability of the episode, the duration of the episode, pre-therapy and post-therapy average atrial and ventricular rates, and the type of therapy delivered.

Typically, in trying to interpret the received arrhythmic information, a physician must look at arrhythmic episodes individually. This makes it difficult for the physician to compare two or more arrhythmic events at the same time, as the physician would have to change between two or more windows in trying to make a comparison. The present invention, in contrast, provides the physician an opportunity to view one or more arrhythmic episodes concurrently through a graphical depiction on the graphical display screen 102 to allow for a more convenient and more accessible way of viewing, interpreting and interacting with the selected arrhythmic episodes.

To accomplish this, the physician selects one or more of the downloaded arrhythmic episodes to graphically display on the interactive display screen 102 at step 124. In one embodiment, the selection of the arrhythmic episodes of interest is made from a list of the plurality of arrhythmic events in the patient's therapy history. In addition to selecting the arrhythmic episodes to view, the physician or clinician also selects at least one arrhythmia analysis criteria at step 126. The arrhythmia analysis criteria allow the physician an opportunity to choose how to view the selected arrhythmic information. In one embodiment, the arrhythmia analysis criteria include, but are not limited to, a similarity/dissimilarity determination, the chronology of occurrences of the arrhythmic episodes, the sensed heart rate of the arrhythmic event, signals from sensor readings, or values, during the arrhythmic event (e.g., impedance, minute ventilation, or accelerometer signals), the time of the day of the arrhythmic event (e.g., circadian occurrence of arrhythmia), morphological similarities, the type of therapy used to treat the arrhythmia, and/or the outcome of the therapy applied to treat the arrhythmia of the heart. The physician or clinician selects the one or more arrhythmia analysis criteria through a display on the interactive display screen 102 of the medical device programmer 60.

Depending upon which arrhythmia analysis criteria were selected in step 126, the medical device programmer 60 then proceeds to process the downloaded cardiac data and display the processed data on the interactive display screen 102. In step 128, the recorded arrhythmic episodes are then graphically depicted on the graphics display screen 102 to allow the physician to compare and assess the selected arrhythmic episodes. In one embodiment, the recorded arrhythmic episodes are represented by symbols displayed on an interactive diagram on the graphics display screen 102. In one embodiment, the symbols represent individual arrhythmic complexes of an arrhythmic episode. In an alternative embodiment, the symbols represent an entire arrhythmic episode. Additionally, the symbols have any number of shapes, including alphabetical or numerical, where a unique shape is used to represent each of the arrhythmic episodes selected for display. Generally, the symbols are used to represent the selected arrhythmic episodes in a convenient interactive diagram. In a further embodiment, colors and/or the shapes of the symbols are used to further distinguish the selected arrhythmic events on the interactive display screen 102.

Figure 5:
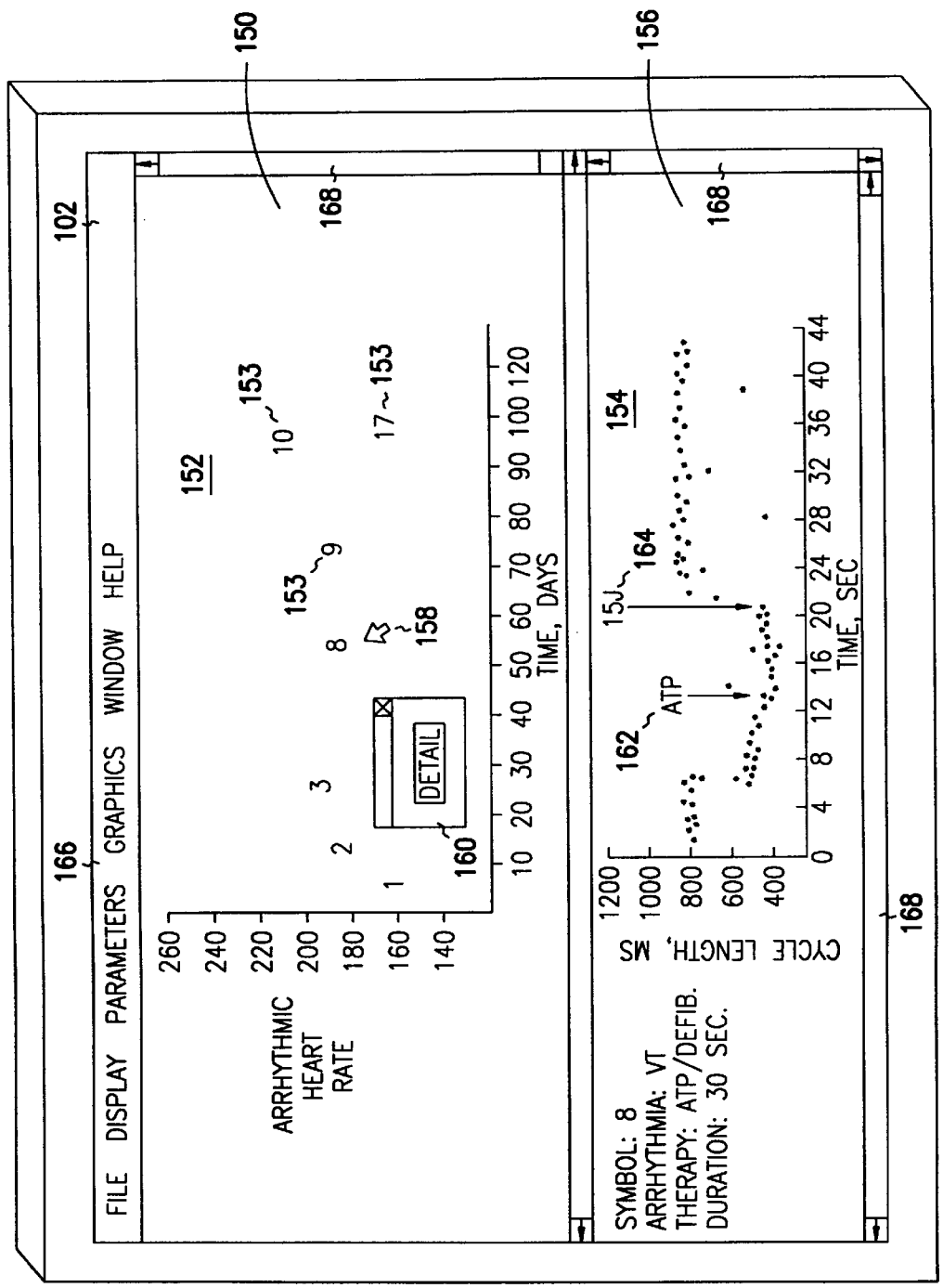
FIG. 5 is a graphical diagram illustrating one embodiment of displaying cardiac arrhythmia data on an interactive display screen.

Referring now to FIG. 5, there is shown one embodiment of selected arrhythmic episodes displayed on the graphical display screen 102. In one embodiment, the physician first interrogates the cardiac defibrillator 20 and selects one or more arrhythmic episodes of interest from the therapy history display. Next, the physician selects one or more arrhythmic analysis criteria, where in the present embodiment the chronological occurrence of the arrhythmic events is chosen to process the selected arrhythmic episodes for display on the graphics display screen 102. Based on this selection, the medical device programmer 60 plots the heart rate of the selected arrhythmic episodes as a function of time in a first viewing window 150.

In this embodiment, the heart rate of the selected arrhythmic episodes is plotted, or mapped, on a Cartesian coordinate system as a function of the day on which the arrhythmic episode occurred. In the present embodiment, arrhythmic episodes 1–3, 8–10 and 17 are displayed on a first diagram 152, where the symbols 153 represent the selected arrhythmic episodes. In the present embodiment, the symbols 153 represent the chronological occurrence of the arrhythmic event, where the number "1" represents the first arrhythmic episode recorded, and the number "17" represents the seventeenth arrhythmic episode recorded by the cardiac defibrillator 20 since being reset by the physician.

In a further embodiment, the interactive display screen 102 of the present invention allows a physician or clinician to elicit explanatory messages about various aspects of the arrhythmic episodes represented by the symbols by using the cursor control device, such as the stylus 104, or, alternatively, a mouse or cursor control buttons. In one embodiment, once a physician or clinician identifies a particular symbol, such as by touching the interactive display screen 102 with the stylus 104, or by a "point and click" action with a mouse, explanatory text about the corresponding sensed arrhythmia and subsequent therapy delivered by the implanted cardiac defibrillator temporarily appears on the screen. In one embodiment, the messages displayed on the interactive display screen 102 are generated by the electronic circuitry of the medical device programmer 60 executing an expert system software as are known in the art.

In an additional embodiment, FIG. 5 also shows a split interactive display screen 102, where a second diagram 154 appears in a second viewing window 156. The split interactive display screen 102 allows additional information relating to the graphically displayed arrhythmic episodes in the first viewing window 150 and information in the second window 156 to be concurrently displayed. The second diagram 154 is requested at the discretion of the physician. In one embodiment, the physician selects one or more of the arrhythmic event symbols displayed in the first diagram 152. The physician then selects the type of additional information to be displayed in the second viewing window 156. In one embodiment, the physician selects from viewing electrocardiogram signals of the selected arrhythmic events, including two or more channels such as ventricular traces and/or atrial traces; the chronological number of the selected episode; the date and time of the selected episode; the type of selected episode detected; the onset rate of the selected episode; the stability of the selected episode; the duration of the selected episode; the pre-therapy and post-therapy average atrial and ventricular rates; and the type of therapy delivered.

In one embodiment of selecting arrhythmic events for which additional information is desired, the physician directs a cursor 158 to an arrhythmic episode of interest on the heart rate as a function of a time plot in the first viewing window 150. In one embodiment, after the physician directs the cursor 158 over an arrhythmic episode symbol, the medical device programmer 60 displays an information window 160 within the first viewing window 150. In one embodiment, the information window 160 prompts the physician to request further details on the chosen arrhythmic episode symbol. Upon choosing to select further details on the arrhythmic episode, the physician is presented with a menu of options for displaying additional information on the arrhythmic event. In one embodiment, the physician chooses from displaying the electrocardiogram of the arrhythmic event, the cycle length or heart rate of the recorded arrhythmic event as a function of time, information related to the type of arrhythmia recorded, the type of therapy provided to convert the arrhythmia, the duration of the arrhythmia, along with any additional data received from the cardiac defibrillator 20. Other information relating to arrhythmic events common in the art is also considered to be within the scope of this additional detail feature of the present embodiment.

After the physician makes the selection of what additional information is to be displayed, the medical device programmer 60 displays the information in the second viewing window 156. In the present embodiment, the additional information requested was the arrhythmic complex cycle length as a function of time. In addition to displaying the graphical representation of the arrhythmic episode on the second diagram 154, additional information related to the number of the arrhythmic episodes chosen, the type of arrhythmia detected, the therapy used in treating the arrhythmia, and the duration of the arrhythmia are also displayed in the second viewing window 152. The graphical representation of the arrhythmic episode 158 is shown as a scatter plot, where the individual points on the graph represent arrhythmic complexes detected during the arrhythmic episode. Also shown in the graphical representation are therapy markers 162 and 164 indicating the type of therapy and the time it was delivered to the heart. In an additional embodiment, the physician has the option of placing the cursor 158 over either therapy marker 162 or 164 to elicit additional information relating to the delivered therapy through additional informational windows appearing on the second viewing window 156.

In addition to the first and second viewing windows, 150 and 156, the graphical display screen 102 also contains a menu bar 166, which contains a variety of functional pull down windows. In one embodiment, the pull down windows of the menu bar allows the patient's cardiac data information to be, for example, saved, altered, printed, edited, and/or displayed. In addition, the menu bar also allows the physician to select additional information on arrhythmic episodes, whether displayed on the first diagram 152 or in the therapy history list. Additionally, the graphical display screen 102 also includes scroll bars 168, which allow the image in the first or second viewing screen to be moved within the viewing screen. In an additional embodiment, additional types of control bars are incorporated into the display screen 102, including ruler bars and other tool bars that are known in the art.

Figure 6:
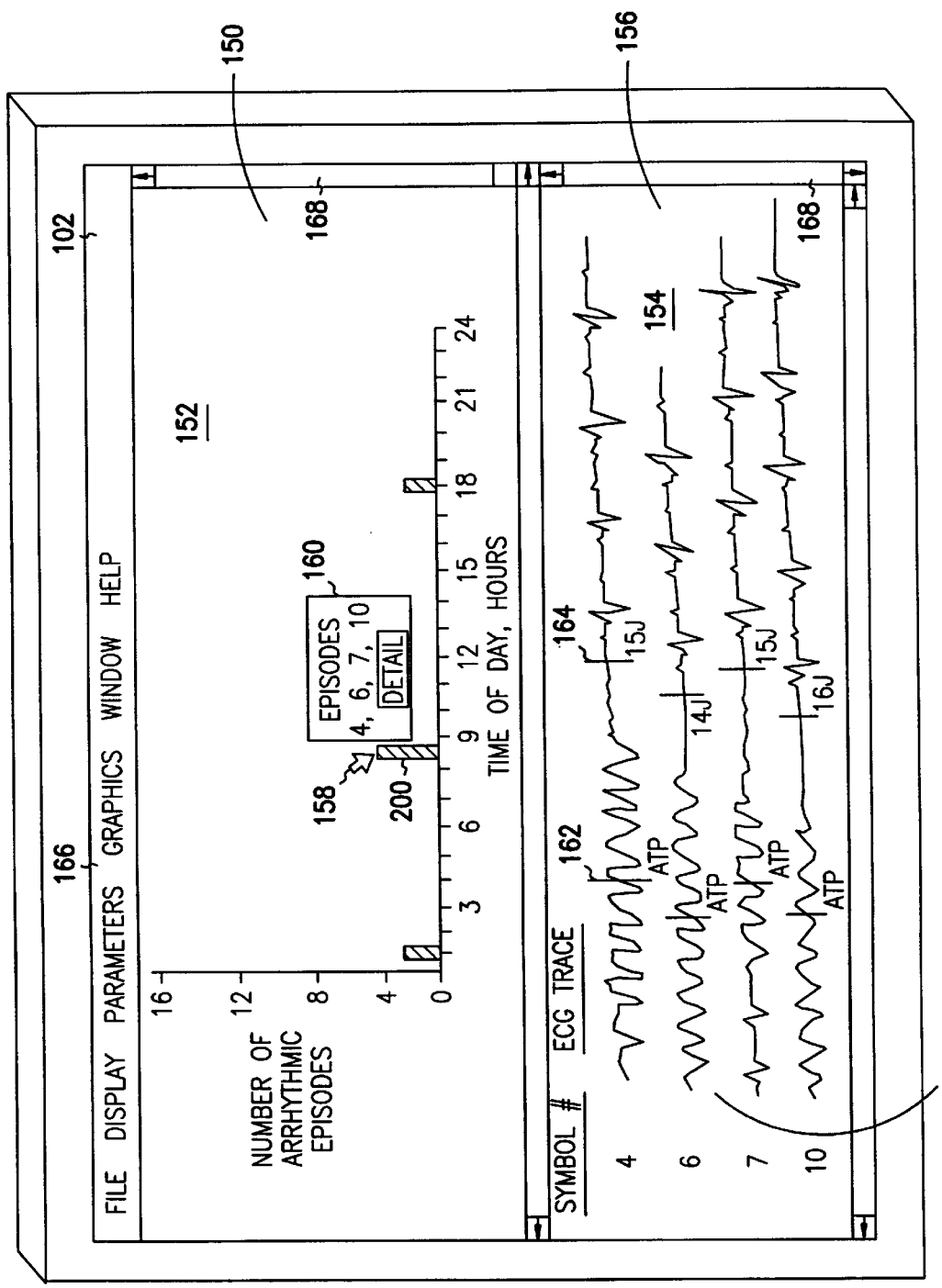
FIG. 6 is a graphical diagram illustrating one embodiment of displaying cardiac arrhythmia data on an interactive display screen.

Referring now to FIG. 6, there is shown an additional embodiment of selected arrhythmic episodes displayed on the graphical display screen 102. In one embodiment, the physician interrogates the cardiac defibrillator 20 and selects one or more arrhythmic episodes of interest from the therapy history display. Next, the physician selects one or more arrhythmia analysis criteria, where in the present embodiment the time of the day of the arrhythmic episode (e.g., circadian occurrence of arrhythmia) is selected to process the selected arrhythmic episodes for display on the graphics display screen 102. Based on this selection, the medical device programmer 60 plots the bars 200 representing the number, or frequency, of arrhythmic episodes that have occurred during a circadian (or a 24-hour) cycle on the first diagram 152.

In one embodiment, additional information about the graphically displayed arrhythmic events is obtained by positioning cursor 158 positioned over bar 200. Bar 200 represents the sum of arrhythmic episodes occurring approximately on the eight day after the patient's cardiac defibrillator 20 was reset by the physician. In one embodiment, placing the cursor 158 over bar 200 causes the medical device programmer 60 to display the informational window 160. In an additional embodiment, the information window 160 displays an informational message related to the arrhythmic episode numbers that are represented by the bar 200. In an additional embodiment, the physician can also request additional information relating to the graphically represented arrhythmias as previously described. In one embodiment, the physician selects electrocardiogram traces 202 for all four of the arrhythmic episodes represented in bar 200 be displayed in the second viewing window 156. The graphical display screen 102 splits to accommodate the number of electrocardiogram traces 202 requested, so that the selected electrocardiogram traces and the graphically displayed arrhythmic episodes are simultaneously displayed. In an alternative embodiment, the fields of the first and second viewing window 150 and 156 scroll via scroll bar 168 to allow the viewing windows to maintain their original size while allowing all requested information to be displayed on either the first or second viewing windows 150 or 152. In an alternative embodiment, the physician selects less than all the arrhythmic events represented by a bar, such as bar 200, to be displayed.

Besides a portion of the patient's electrocardiogram being displayed on the interactive display screen 102, the medical device programmer 60 also includes therapy markers 162 and 164 symbolically displaying the occurrence of the therapy delivered to the arrhythmic heart, and the subsequent electrocardiogram of the patient after the therapy. In an additional embodiment, the physician has the option of placing the cursor 158 over either therapy markers 162 or 164 to elicit additional information relating to the arrhythmic episode characteristics and the delivered therapy through additional informational windows appearing on the second viewing window 156. Additionally, the second viewing window 156 also shows the subsequent cardiac rhythm after the delivery of therapy. In an additional embodiment, the physician is able to elicit information regarding the sensed heart rate of the arrhythmic event, signals from sensor readings, or values, during the arrhythmic event (e.g., impedance, minute ventilation, or accelerometer signals), the time of the day of the arrhythmic event, the type of therapy used to treat the arrhythmia, and/or the outcome of the therapy applied to treat the arrhythmia of the heart.

In addition to the first and second viewing windows, 150 and 156, the graphical display screen 102 also contains a menu bar 166, which contains a variety of functional pull down windows. In one embodiment, the pull down windows of the menu bar allows the patient's cardiac data information to be, for example, saved, altered, printed, edited, and/or displayed. In addition, the menu bar also allows the physician to select additional information on arrhythmic episodes, whether displayed on the first diagram 152 or in the therapy history list. Additionally, the graphical display screen 102 also includes scroll bars 168, which allow the image in the first or second viewing screen to be moved within the viewing screen. In an additional embodiment, additional types of control bars are incorporated into the display screen 102, including ruler bars and other tool bars that are known in the art.

In an additional embodiment, selected arrhythmic episodes are analyzed and plotted on the interactive display screen based on the morphological characteristics of the arrhythmic episode complexes. In one embodiment, the medical device programmer calculates a morphological metric value for each complex of an arrhythmic episode. The morphological metric value is based on predetermined morphology characteristics of each complex and predetermined morphology characteristics of normal sinus rhythm complexes. By making a functional comparison of the arrhythmic complex morphology and the normal sinus rhythm complex morphology, a morphological metric value for each arrhythmic complex is calculated. Symbols representing the arrhythmic complexes are then plotted as a function of the morphological metric values on an interactive display screen.

Figure 7:
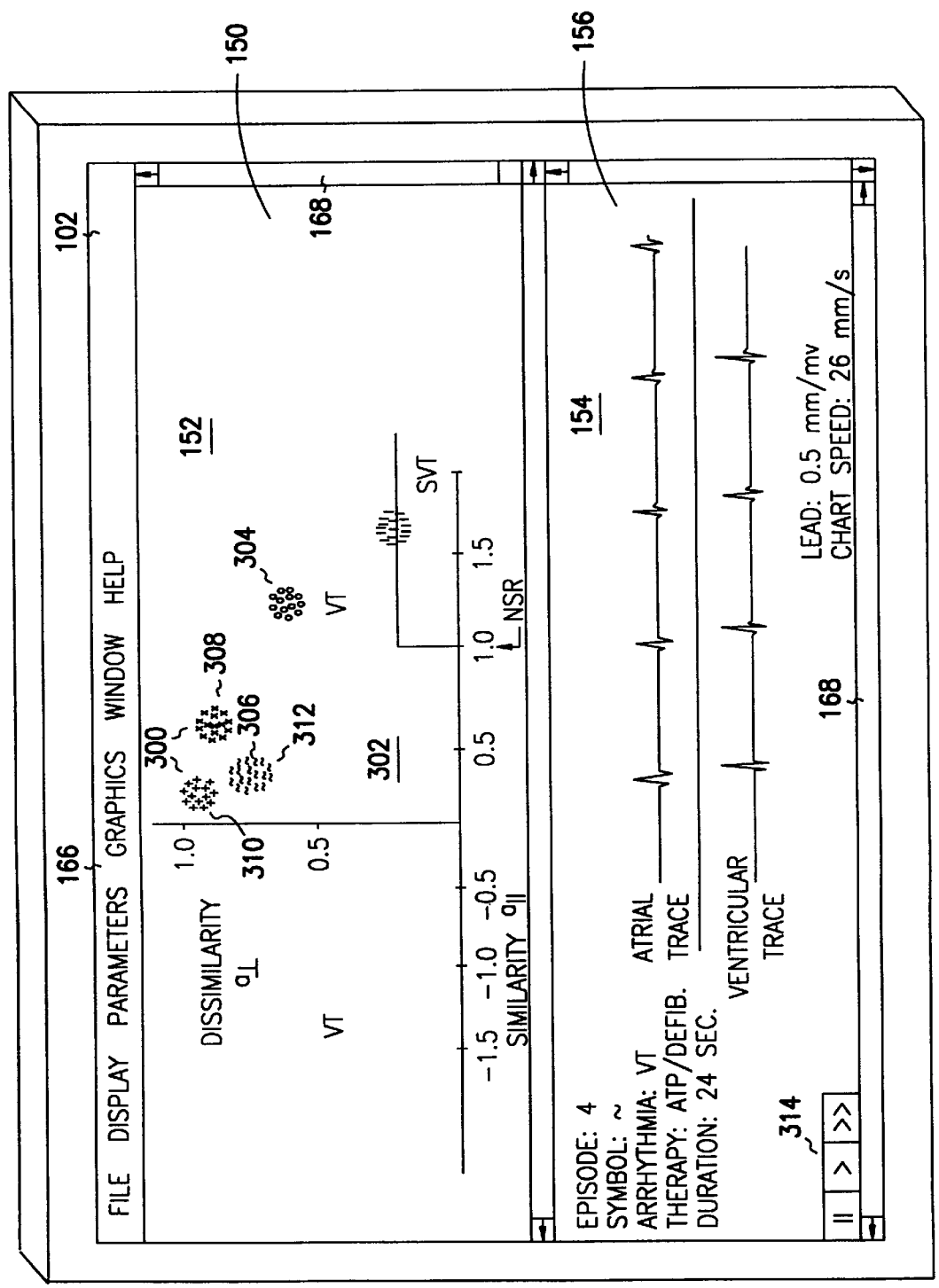
FIG. 7 is a graphical diagram illustrating one embodiment of displaying cardiac arrhythmia data on an interactive display screen.

Referring now to FIG. 7, there is shown an embodiment of analyzing and plotting arrhythmic episodes as a function of the morphological characteristics of the arrhythmic episodes. In one embodiment, the physician first interrogates the cardiac defibrillator 20 and selects one or more stored arrhythmic episodes of interest from the plurality of arrhythmic episodes displayed in the therapy history display. Next, the physician selects one or more arrhythmic analysis criteria, where in the present embodiment the similarity/dissimilarity determination is chosen to process the selected arrhythmic episodes for display on the graphical display screen 102. In one embodiment, the similarity/dissimilarity determination calculates for the morphological metric value a similarity value and a dissimilarity value for each complex of an arrhythmic episode with respect to normal sinus rhythm complexes.

The medical device programmer 60 determines similarity and dissimilarity values for arrhythmic complexes of selected arrhythmic episodes. In one embodiment, the similarity values and the dissimilarity values are determined from the QRS wave morphology of the recorded electrocardiogram received from the cardiac defibrillator 20. For each arrhythmic complex a similarity and dissimilarity value are calculated. A symbol 300 is then generated for the arrhythmic episode, and each of its plurality of arrhythmic complexes, which is plotted on a similarity/dissimilarity plane 302 as a function of the calculated similarity values and the dissimilarity values in the first viewing window 150 of the interactive display screen.

In one embodiment, the symbol 300 representing arrhythmic complexes are assigned an individualized shape and/or color to represent an entire arrhythmic episode. Symbols 300 representing the complexes of an arrhythmic episode typically form clusters 304 due to the morphological similarity of the arrhythmic complex signals making up the arrhythmic episode. So, in one embodiment, the symbol "~" represents the arrhythmic complexes of arrhythmic episodes 306.

In one embodiment, the symbols 300 to assists the physician in distinguishing one cluster 304 of symbols 300 representing an arrhythmic episode from other cluster plotted on the similarity/dissimilarity plane 302. Two or more clusters that are very close on the similarity/dissimilarity plane, such as clusters 308, 310, and 312 indicates that the arrhythmic episodes represented by the clusters are morphologically similar. The greater the distance between two or more clusters indicates that the arrhythmic episodes represented by the clusters are morphologically less similar.

In an additional embodiment, the physician selects to change the view of the arrhythmic episodes from symbols representing arrhythmic complexes to a single symbol displayed on the similarity/dissimilarity plane which represents an average or mean value of the similarity values and dissimilarity values. In one embodiment, the single symbol is the chronological number of the arrhythmic episode in the therapy history display. In an alternative embodiment, if the symbols of two or more arrhythmic episodes overlap on the similarity/dissimilarity plane 302, the physician is able to use the menu bar to request that the symbols 300 of an arrhythmic event of interest be distinguished from the other symbols by increasing the brightness of the displayed symbols of interest, while dimming the other symbols on the display. In an additional embodiment, when two or more clusters of symbols are overlapping the physician can requests that one or more of the overlapping clusters be temporarily removed so the clusters of the episodes of interest can be viewed more clearly. Additionally, the physician is able to use either an on screen information window, as previously described, or the menu bar 166 to remove or add arrhythmic episodes to the similarity/dissimilarity display 302.

In one embodiment, the physician selects a symbol 300 representing an arrhythmic complex on the similarity/dissimilarity plane 302, and in response the medical device programmer 60 displays an informational window. As previously described, the physician is able to request and display an informational message related to the type of arrhythmia and the therapy regimen provided to treat the selected arrhythmic episode on the interactive display screen. In an alternative embodiment, the physician is able to select two or more symbols 300 representing different arrhythmic episodes for which informational messages, requested through the information window, are concurrently displayed on the interactive display screen 102. Additionally, the physician is able to add information or remove information from the message. Also from this window, the physician is able to request a change in the cardiac defibrillator 20 programmable parameters, return to the selected graphical display, or to the therapy history list.

As previously described, the physician uses the information window 160 to elicit further information about one or more of the received arrhythmic episodes. In one embodiment, the physician is able to request and display one or more electrocardiogram signal channels of a selected arrhythmic episode in the second view screen 156 of the interactive display screen. In the present embodiment, both an atrial trace and a ventricular trace are shown in the second diagram 154 in the second viewing window 156. In an alternative embodiment, the physician is able to choose to view only the ventricular electrocardiogram channel of the selected arrhythmic episodes.

In one embodiment, the physician plays, pauses or moves through the electrocardiogram traces through the use of buttons 314 displayed on the second view screen 156. Additionally, the physician selects to view additional information, along with the electrocardiogram traces, such as the number of the episode, the symbol of the episode, the type of arrhythmia being displayed, the therapy delivered to treat the arrhythmia, and the duration of the episode. In an additional embodiment, addition information related to the arrhythmic event can also be selected and displayed on the interactive display screen 102.

After receiving instructions on which arrhythmic episodes to display, the medical device programmer 60 calculates a similarity value and a dissimilarity value for each of the arrhythmic complexes of the selected arrhythmic episodes. In one embodiment, the medical device programmer 60 processes the plurality of complexes of the selected arrhythmic episodes to derive an arrhythmic vector, A, based on received electrocardiogram signals for each complex of the plurality of complexes. In one embodiment, the medical device programmer 60 determines the arrhythmic vector, A, based on predetermined waveform characteristics of cardiac QRS-waves recorded during the arrhythmic episode.

One way of deriving arrhythmic vectors is by recording waveform characteristics at predetermined morphological points along each of the complexes. In one embodiment, the waveform characteristics are extracted amplitudes of peaks and valleys (or maxima and minima) in the QRS wave of each arrhythmic complex through a process called feature extraction. Each arrhythmic complex is isolated according to a known morphological template. In one embodiment, the morphological template operates to detect the activation of an heart beat (such as the occurrence of an R-wave), at which point the programmer electronic circuitry analyzes the complex associated with the signal indicating the activation of the heart beat. In one embodiment, a threshold value or a detection criterion, as known in the art, is used to indicate the activation of the heart beat. The resulting arrhythmic vector includes a set of numbers, each number associated with a particular morphological point of the complex. The arrhythmic vector values associated with each arrhythmic complex are then stored in the medical device programmer.

Each arrhythmic vector is then compared with a normal rhythm vector, N, representing the patient's QRS complex during normal sinus rhythm. In one embodiment, the normal rhythm vector, N, is determined from predetermined waveform characteristics of cardiac QRS-waves recorded during normal sinus rhythm. In one embodiment, this information is obtained from the normal sinus rhythm snapshot. The resulting normal rhythm vector, N, includes a set of numbers, each number associated with a particular morphological point of the normal sinus rhythm. The programmer electronic circuitry then compares each arrhythmic vector with the normal rhythm vector to calculate a similarity value and a dissimilarity value for each arrhythmic vector relative the patient's normal sinus rhythm.

Figure 8:
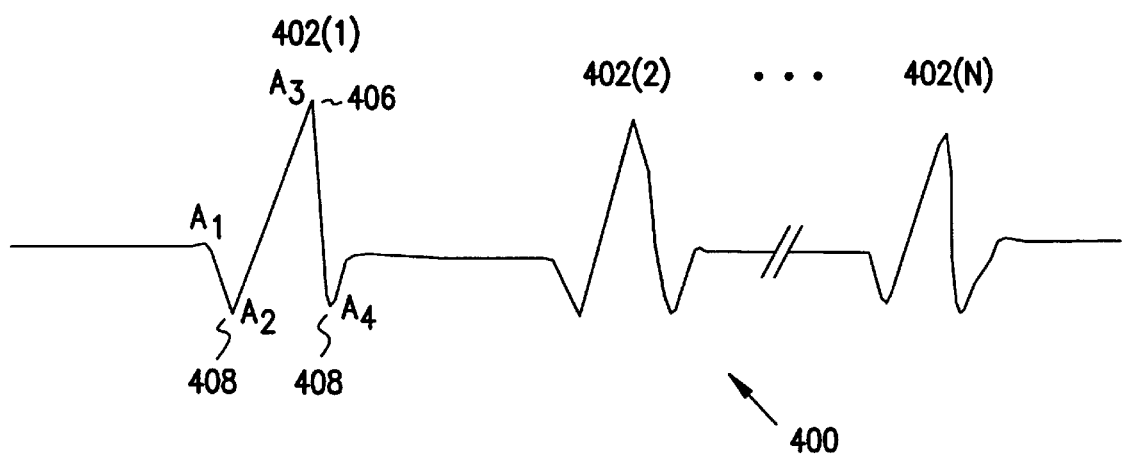
FIG. 8 is one embodiment of an electrocardiogram signal recorded during an arrhythmic episode.

Referring now to FIG. 8, there is shown one embodiment of an arrhythmic episode electrocardiogram 400. The typical cardiac arrhythmia comprises a series of arrhythmia complexes 402(1), 402(2), ... 402(N) as shown in FIG. 8. In one embodiment, the medical device programmer 60 determines a similarity value and a dissimilarity value for each of the arrhythmia complexes by analyzing the individual QRS waves 404 of the arrhythmic complexes relative the patient's normal sinus rhythm. The arrhythmia complexes are processed by the medical device programmer 60 to determine the amplitudes of peaks 406 and valleys 408 in the QRS complex 404 of the arrhythmia complexes 402(1), 402(2) ... 402(N). In one embodiment, the peaks 406 and valleys 408 are determined by determining major inflection points in the QRS complex.

The resulting values of the peaks 406 and valleys 408 provides a four dimensional arrhythmic vector, A=[A1, A2, A3, A4], representing each of the arrhythmic complexes. In an additional embodiment, the medical device programmer 60 analyzes the "snapshot" of normal sinus rhythm to determine average amplitudes of peaks and valleys for the QRS complex of the patient's normal sinus rhythm. From these values a four dimensional normal rhythm vector, N=[N1, N2, N3, N4], for normal sinus rhythm is determined. The two vectors A and N are then used to determine values for the similarity and dissimilarity for each of the arrhythmic complexes. A symbol representing similarity of each arrhythmic vector to the normal rhythm vector is then mapped on the interactive display screen. In one embodiment, the similarity and dissimilarity values of the arrhythmic complexes are then plotted on a discrimination plane 302 (e.g., as in FIG. 7). In one embodiment, a discrimination plane is defined by the two-dimensional plane created by the vectors N/|N| and A/|N|, where the orthogonal axises of the discrimination plane are defined by the similarity feature values (a∥) and the dissimilarity feature values (a⊥).

Similarity and dissimilarity feature values are then calculated for the A/|N| vector, where the feature values designated as a∥ and a⊥ are the components of the vector A/|N| parallel and perpendicular, respectively, to the N/|N| vector. The component a∥ represents the degree with which the arrhythmic vector A/|N| is similar to the non-arrhythmic vector N/|N|. This value is obtained by taking the projection (dot product) of the arrhythmic vector A/|N| onto the non-arrhythmic vector N/|N|, which has the units of length. So, the similarity value, a∥, is determined by the equation [A·N]/[N·N]. Thus, the feature value a∥ is the similarity feature of the vector A/|N| with respect to the vector N/|N|. The component a⊥ represents the degree with which the arrhythmic vector A/|N| is dissimilar to the non-arrhythmic vector N/|N|. This value is obtained by taking the projection of the vector A/|N| onto the vector in the discrimination plane which has the unit of length, and which is perpendicular to the vector N/|N|. So, the dissimilarity value, a⊥, is determined by the equation $SQRT[(A \cdot A)/(N \cdot N) - (a\perp)^2]$. Thus, the value a⊥, is the dissimilarity feature of the vector A/|N| with respect to the vector N/|N|.

Figure 9:
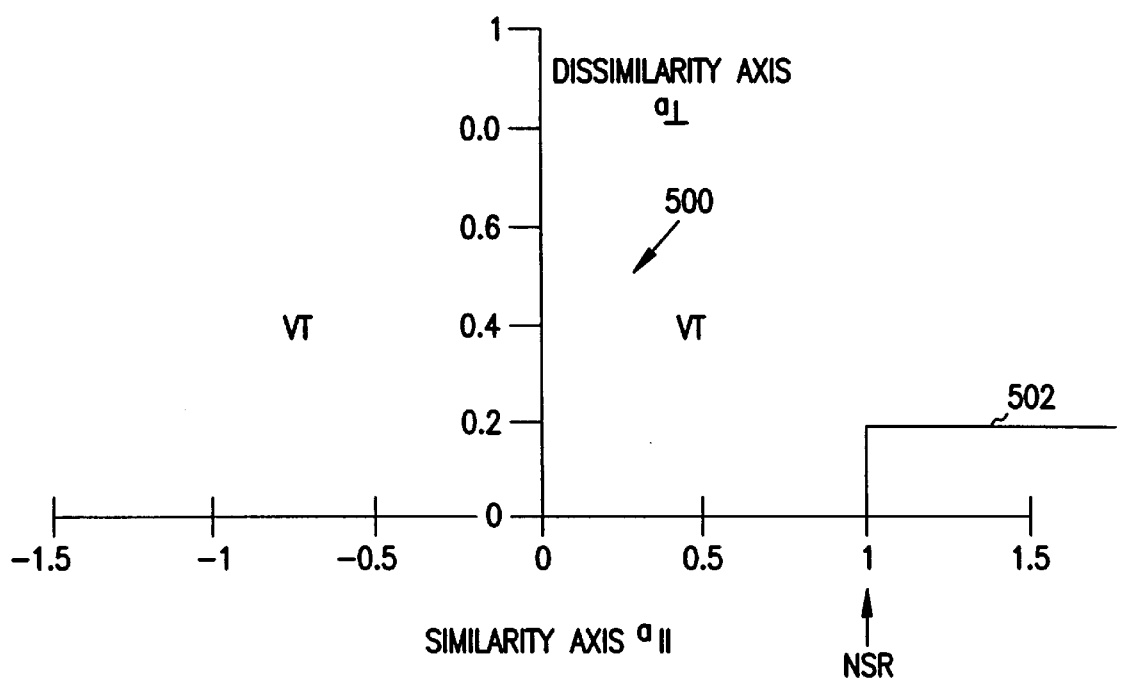
FIG. 9 is one embodiment of a similarity/dissimilarity plane.

Referring now to FIG. 9, there is shown an embodiment of the similarity/dissimilarity plane 500. As previously stated the similarity/dissimilarity plane 500 is defined by the two-dimensional plane created by the vectors N/|N| and A/|N|, where the orthogonal axises of the discrimination plane are defined by the similarity feature values (a∥) and the dissimilarity feature values (a⊥). In addition to displaying symbols representing the complexes of an arrhythmic episode, the similarity/dissimilarity plane is also used to classify the arrhythmic episode as a ventricular tachycardia (VT) episodes or a non-VT episodes. FIG. 9, shows the similarity/dissimilarity plane 500 having orthogonal axes a∥ and a⊥, which are referred to as the similarity and dissimilarity coordinate axes.

In an additional embodiment, the physician is able to define one or more notice regions on the discrimination plane through the interactive display screen. In one embodiment, FIG. 9 displays an example of a notice region 502 surrounding the baseline point (1.0, 0.0). Arrhythmic episodes which fall into the notice region 502 are morphologically similar to normal sinus rhythm, but have a cardiac rate that exceeds that of normal sinus rhythm. In one embodiment, arrhythmic episodes that fall within notice region 502 are classified as supraventricular tachyarrhythmias and are not necessarily life threatening. The area falling outside of the notice region 502 is considered to represent ventricular tachycardia activity (or VT region), and arrhythmia complexes falling in this area are considered to represent an ventricular tachycardia arrhythmic episode. Therefore, plotting the arrhythmic complexes on the similarity/dissimilarity plane 500 assists the physician in making a determination of the type of arrhythmias experience by the patient.

In one embodiment, the physician creates a notice region on the discrimination plane through the use of the user input device, such as the stylus 104. In an alternative embodiment, the boundary separating the notice region 502 and the VT regions within the similarity/dissimilarity plane 500 is predetermined by testing a population of patients, and essentially does not change from individual to individual. In an alternative embodiment, the physician is able to change the shape and position of the notice region 502 through the use of the menu bars 166 and the interactive display screen 102. The position of the one or more notice regions 502 are then retrievably stored.

The physician is then able to plot, or map, one or more symbols representing selected arrhythmic events on the discrimination plane. In one embodiment, the medical device programmer 60 issues an advisory message or an alert on the interactive display screen 102 if at least one symbol is plotted within one or more notice regions on the interactive display. In one embodiment, only the arrhythmic events that were selected by the physician are tested against the one or more notice regions. In an additional embodiment, the medical device programmer 60 is programmed to automatically determine if any of the received arrhythmic episodes fall on or within a notice region. One reason for this is to alert the physician to a recorded arrhythmic event that may not have been selected, but yet would fall within a notice region of the graphical display.

In an additional embodiment, the physician is able to create one or more notice regions on the interactive display screen 102. For example, the physician selects an area on the similarity/dissimilarity plane 500 that will cause the medical device programmer to issue an advisory message or alert when one or more complexes from an arrhythmic episode fall on or within the notice region. In one embodiment, the physician uses the cursor control device, such as the stylus 104, or, alternatively, a mouse or cursor control buttons, to draw the one or more notice regions on the interactive display screen 102. In one embodiment, as the physician is drawing a notice region, the interactive display screen 102 creates a line along the path drawn by the physician to indicate the shape and location of the notice region on the similarity/dissimilarity plane 500. In one embodiment, the one or more notice regions are then retrievably stored for use in connection with the patient's cardiac defibrillator 20. Additionally, the physician sets conditions or rules with respect to the similarity/dissimilarity plane 500 that would highlight or remind the physician of some condition that the physician wants to be reminded of with regards to the particular patient.

In an additional embodiment, the physician programs the medical device programmer 60 not only to signal an advisory notice if any of the received arrhythmias occur within a notice region or area of the similarity/dissimilarity plane 500, but also to provide a message, or textual notes, relating to the notice region. In one embodiment, the textual notes and/or messages are recalled either by directing the cursor 158 over the line defining the notice region, or through the menu bar. In one embodiment, the message relates to the type of arrhythmia encountered in the particular portion of the similarity/dissimilarity plane 500. Additionally, the message relates to the type of therapy that has been attempted in trying to treat the arrhythmia found in this area. Additionally, other messages pertaining to and important for the notice region can also be included.

In addition, the physician is able to assess the effectiveness of the therapy delivered for the type of arrhythmias encountered by the cardiac defibrillator 20. Also, the physician is able to use the similarity/dissimilarity plane 500 to assess the recurrence of arrhythmic episodes that were either treated surgically or are being treated pharmaceutically.

Figure 10:
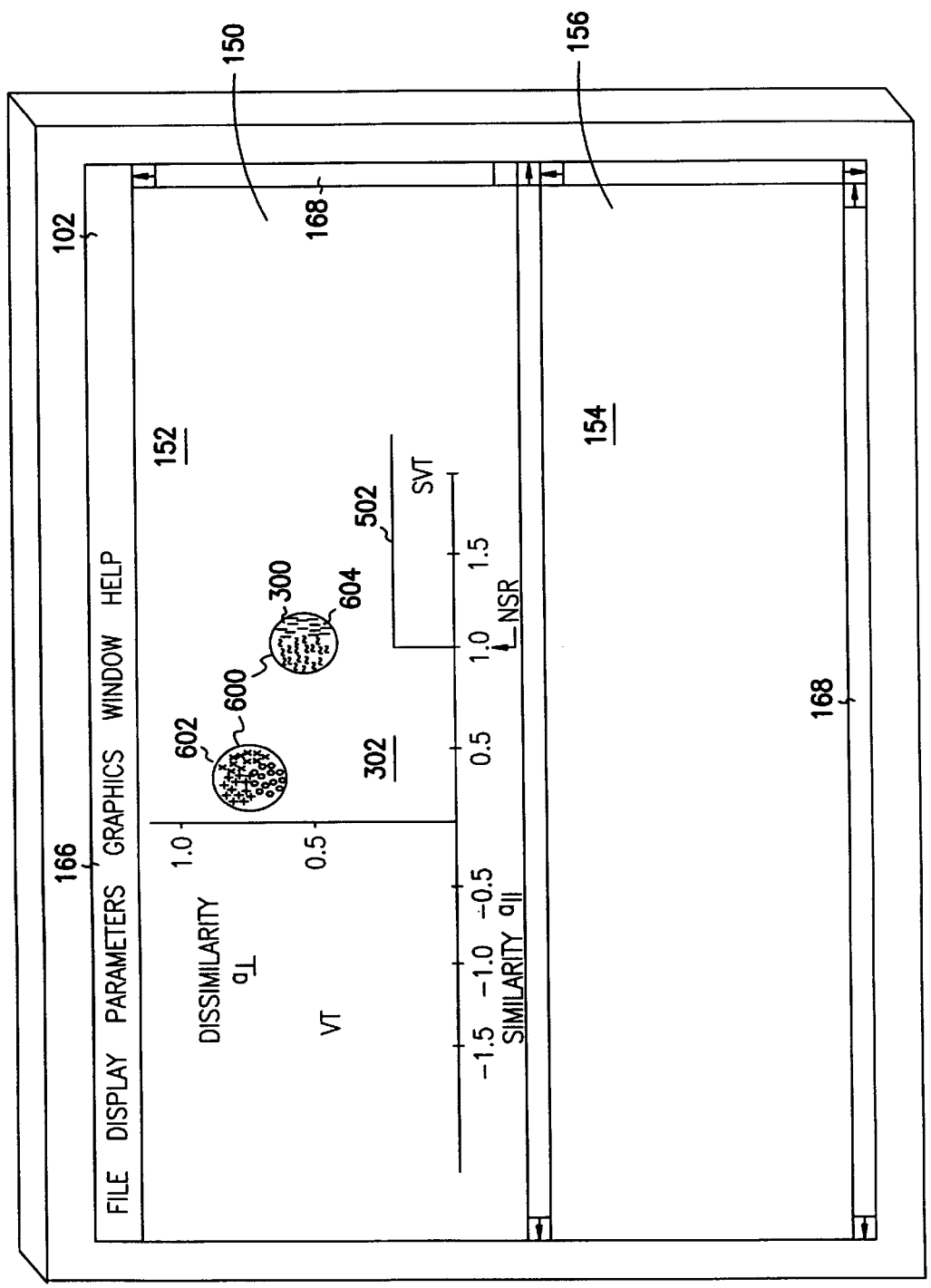
FIG. 10 is a graphical diagram illustrating one embodiment of displaying cardiac arrhythmia data on an interactive display screen.

Referring now to FIG. 10 there is shown an additional embodiment of the present invention. In additional to graphically displaying the symbols 300 of arrhythmic complexes on the similarity/dissimilarity plane 302, the physician is also able to selectively group the symbols 300 of one or more arrhythmic episodes within a defined boundary 600 on the interactive display screen 102. In one embodiment, the physician draws the defined boundary 600 around the symbols of interest using the interactive display screen 102. In one embodiment, the physician uses either the information window 160, or the menu bar 166, to set the medical device programmer 60 to accept the creation of a defined boundary. The medical device programmer 60 displays a line indicating where the defined boundary 600 is being drawn as the physician inputs the information on the interactive display screen 102. In one embodiment, the physician creates the defined boundary to encircle one or more arrhythmic complexes.

In one embodiment, the physician encircles one or more symbols 300 representing one or more arrhythmic episodes through the use of the graphics display screen 102 with the stylus 104, or even the user's finger. In an alternative embodiment, the physician encircles the one or more symbols 300 through the use of the computer "mouse"-type pointing device, rather than the stylus 104. In one embodiment, the physician encircles complexes representing entire arrhythmic episodes. In an alternative embodiment, the physician encircles only a portion of the displayed arrhythmic complex symbols by the boundary.

After drawing the defined boundaries, the physician is able to retrievably store the boundary positions on the similarity/dissimilarity plane 302 for use during the current patient visit or during a subsequent patient visit. Additionally, the physician is able to recall the location of one or more of the saved boundaries at a later time. In one embodiment, this allows the physician to determine if subsequent arrhytmic episodes fall into one or more of the boundaries 600. In one embodiment, the lines used to represent the boundaries are displayed using individual colors and/or having symbols around the perimeter of the line to distinguish one boarder from another boarder. In one embodiment, a window containing a key to the boarder color or symbols is provided to assist the physician in distinguishing the boarders.

FIG. 10 shows a first arrhythmic cluster 602 and a second arrhythmic cluster 604 encircled by defined boundaries 600. FIG. 10 also shows the notice region 502. The defined boundaries 600 encircling the first arrhythmic cluster 602 and the second arrhythmic cluster 604 are retrievably stored either in the medical device programmer, the implantable medical device, or in a removable storage medium, such as a floppy disk.

During a patient visit, the physician interrogates the cardiac defibrillator 20 to download, or receive, the patient's cardiac data relating to arrhythmic episodes. The physician is then able to request that the medical device programmer 60 recall the defined boundaries 600 that were "learned" or stored on the similarity/dissimilarity plane 302 during the patient's last visit. In one embodiment, the physician requests that the medical device programmer analyze the downloaded cardiac data to determine if any of the complexes of the arrhythmic episodes fall within any of the defined boundaries 600 on the similarity/dissimilarity plane 302. In an alternative embodiment, the physician selects arrhythmic events to plot, or map, on the similarity/dissimilarity plane 302 for the purpose of determining if any of the selected arrhythmic events fall within the boundaries 600.

In an additional embodiment, the medical device programmer 60 also determines and stores a representative electrocardiogram signal for the one or more arrhythmic episodes contained within the defined boundaries. In one embodiment, this representative electrocardiogram is an average electrocardiogram derived from the arrhythmic complexes located within the defined boundary 600. In an alternative embodiment, the representative electrocardiogram is the electrocardiogram of the arrhythmic event that is most centrally located within the defined boundary 600. The physician, viewing one or more of the defined boundaries, can then select one or more of the defined boundaries and request that the stored representative electrocardiogram signal of the selected defined boundaries be displayed on the interactive display screen 102.

In an additional embodiment, the defined boundaries 600 can be altered by the physician based on additional information that is plotted on the similarity/dissimilarity plane 302. In one embodiment, the physician alters a boundary to include additional complexes of a newly plotted arrhythmic event. In an alternative embodiment, the physician alters a boundary to decrease the size of the boundary. In one embodiment, changing the boarder also causes the representative electrocardiogram to be changed as well.

In an additional embodiment, the electronic control circuitry of the medical device programmer is programmed to automatically determine distinct groupings of complexes representing arrhythmic episodes and to provide defined boundaries around the periphery of the detected groups or clusters of symbols. In one embodiment, the symbols are grouped by the programmer electronic circuitry within a defined boundary based upon the morphological similarity of the arrhythmic complexes.

In one embodiment, the grouping of the arrhythmic complexes is accomplished by comparing average similarity values and average dissimilarity values for pairs of arrhythmic episodes. In one embodiment, the magnitude of the arrhythmic vector difference between a first arrhythmic complex and a second arrhythmic complex is calculated. If the difference of the average similarity values is greater than or equal to a lower grouping threshold value and less than an upper grouping threshold value and the difference of the average dissimilarity values is greater than or equal to the lower grouping threshold value and less than the upper grouping threshold value then the first arrhythmic event and the second arrhythmic event are sufficiently similar to group the two arrhythmic complexes. This same procedure is repeated for subsequent pairs of arrhythmic complexes. In one embodiment, the lower grouping threshold value is programmed in a range between 0.0 and 0.1 and the upper grouping threshold value is programmed in a range between 0.0 and 0.1. Based on this type of calculation the medical device programmer 60 groups arrhythmic complexes to be encircled by one or more boundaries 600.

Also, based on a patient's recorded arrhythmic episodes, a physician may decide to perform surgery in an attempt to prevent future occurrences of a particular type of observed arrhythmic episode. In one embodiment, the physician uses the boundaries 600 to assess the success of treating the patient cardiac arrhythmias. In one embodiment, the physician, after discovering the occurrences of particular arrhythmias, creates one or more defined boundaries around the arrhythmic episodes of interest. In one embodiment, one or more defined boundaries are designated as notice boundaries. The physician then treats the patient's arrhythmia using, for example, surgery and/or pharmaceuticals. The physician then uses the stored boarders to determine if any post/surgery/post-treatment arrhythmic episodes fall within the stored boarder areas, or notice boundaries, that instigated the corrective treatment initially. During the next visit the physician recalls the notice boundaries and queries the medical device programmer to determine if any of the recorded arrhythmic episodes fall within the notice boundaries. In one embodiment, the medical device programmer displays a notice on the interactive display screen if at least one symbol is plotted within one or more notice boundaries on the interactive display screen. In an alternative embodiment, the physician requests to view both selected arrhythmic episodes along with notice boundaries and/or defined boundaries from previously recorded arrhythmic episodes. In this way the physician is able to determine the success of the surgery in treating the arrhythmic episodes of interest.

In an additional embodiment, the physician also stores additional information with the notice boundaries. In one embodiment, the arrhythmic episodes that lead to the creation of the boundary are stored along with the boundary. In an additional embodiment, textual messages and/or the arrhythmic data associated with each of the arrhythmic events is stored. In one embodiment, the type of information that is stored includes the electrocardiogram signals, the chronological number of the episode, the date and time of the episode, the type of episode detected, the onset rate of the episode, the stability of the episode, the duration of the episode, pre-therapy and post-therapy average atrial and ventricular rates, and the type of therapy delivered.

In an additional embodiment, the physician is also able to look at the onset of the grouped arrhythmias. In one embodiment, this information allows the physician to determine a patten of onset for particular types of arrhythmias. In turn, this would allow the physician to program the cardiac defibrillator to, once a known onset pattern was detected, to provide therapy to avoid the arrhythmia by early treatment of the pending arrhythmic episode. In one embodiment, the cardiac defibrillator could provide anti-tachycardia pacing to the ventricles or provide low level cardioversion shocks to the heart in an effort to prevent a more serious arrhythmic episode from occurring. In this manner, the cardiac defibrillator would also be able to conserve power and prolong the life of the battery. Additionally, the onset could signal the cardiac defibrillator to begin to prepare to provide treatment to the impending arrhythmic episode. This would allow for the cardiac defibrillator 20 to be prepared to deliver therapy to the heart very shortly after the beginning of the arrhythmic episode.

In an additional embodiment, the physician uses the interactive display screen 102 to make programming changes in the cardiac defibrillator. Based on the displayed arrhythmic events, the physician programs the type of therapy to be delivered next time the cardiac defibrillator encounters an arrhythmia similar to the one displayed on the interactive diagram 102. In one embodiment, the physician instructs the cardiac defibrillator to deliver a particular type of therapy if an arrhythmic episode falls within a particular region or area of the similarity/dissimilarity plane 302. This information is translated by the medical device programmer 60 into specific changes in the programmable parameters which are then delivered to the cardiac defibrillator 20.

In an additional embodiment, the medical device programmer 60 performs a simulation on the received cardiac data using hypothetical or proposed cardiac defibrillator parameters. In one embodiment, after the physician has received and displayed cardiac data on the interactive display screen, he or she may determine or identify one or more of the sensed arrhythmic episodes that were inappropriately or mistakenly treated by the cardiac defibrillator 20. In one embodiment, the physician could use the interactive display screen to designate one or more regions on the first diagram 152 as areas (i,e., arrhythmias) that should not be treated by the cardiac defibrillator. In one embodiment, this information would then be translated into programming signals to change the programming of the cardiac defibrillator 20.

In an alternative embodiment, instead of programming the cardiac defibrillator 20 to alter the therapy provided to an arrhythmic episode, the medical device programmer 20 simulates the resulting therapy delivered to the received cardiac data when one or more cardiac defibrillator 20 parameters are changed within the medical device programmer 60. In one embodiment, the physician is able to simulate changing any of the programmable settings in cardiac defibrillator 20. The parameters to be changed include, but are not limited to, the rate threshold value, the stability analysis threshold or other programmable parameters. This allows the physician to simulate in the medical device programmer 60 the effect of changing at least one cardiac defibrillator parameter on the cardiac data received from the cardiac defibrillator 20 to determine if appropriately treated arrhythmias would continue to receive treatment and mistakenly treated arrhythmia would no longer, or fail, to receive treatment under the simulation in the medical device programmer 20. In one embodiment, the programmer electronic circuity simulates the effect of the changed cardiac defibrillator parameter using the retrieved cardiac data, and indicates if appropriately treated arrhythmias would have received treatment and mistakenly treated arrhythmia would have fail to receive treatment under the simulation in the medical device programmer 60. In this way, the physician can better determine what the effect of changing the parameter will be before the patient leaves the office.

In one embodiment, this what-if type of analysis allows the physician to save time by providing the results of simulation based on the received cardiac data if a particular parameter were set differently. This also allows the physician to determine if changing the cardiac defibrillator parameter 20 will also adversely effect the therapy of arrhythmias that were properly treated.

We claim:

1. A medical device system, comprising:

a cardiac defibrillator including electronic control circuitry for determining the occurrence of an arrhythmic episode of a heart;

a medical device programmer having programmer electronic circuitry coupled to an interactive display screen and the electronic control circuitry of the cardiac defibrillator, where at least one cardiac defibrillator parameter is changed in the medical device programmer, the programmer electronic circuity simulates the effect of the changed cardiac defibrillator parameter using cardiac data received from the cardiac defibrillator, and indicates if appropriately treated arrhythmias would have received treatment and mistakenly treated arrhythmia would have fail to receive treatment under the simulation in the medical device programmer.

2. A medical device programmer, comprising programmer electronic circuitry for displaying a plurality of symbols, each symbol representing an entire arrhythmic episode, where each symbol is plotted on an interactive display screen as a function of time.

3. The medical device programmer of claim 2, where a plurality of arrhythmic episodes are selected through the interactive display screen.

4. The medical device programmer of claim 2, where each symbol is plotted in chronological order.

5. The medical device programmer of claim 2, where each symbol is plotted as a function of circadian occurrence.

* * * * *